(12) United States Patent
Cheng et al.

(10) Patent No.: US 12,213,723 B2
(45) Date of Patent: Feb. 4, 2025

(54) CONTROLLED COEFFICIENT OF THERMAL EXPANSION VITREOUS ENAMEL COMPOSITION FOR ELECTROSURGICAL TOOL

(71) Applicant: Medtronic Advanced Energy LLC, Minneapolis, MN (US)

(72) Inventors: Xiaoming Cheng, Keller, TX (US); Himanshu K. Bhatt, Keller, TX (US); Zahedul Huq, Keller, TX (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1288 days.

(21) Appl. No.: 16/334,233

(22) PCT Filed: Nov. 14, 2017

(86) PCT No.: PCT/US2017/061615
§ 371 (c)(1),
(2) Date: Mar. 18, 2019

(87) PCT Pub. No.: WO2018/090041
PCT Pub. Date: May 17, 2018

(65) Prior Publication Data
US 2019/0380767 A1    Dec. 19, 2019

Related U.S. Application Data

(60) Provisional application No. 62/421,895, filed on Nov. 14, 2016.

(51) Int. Cl.
*A61B 18/14*    (2006.01)
*A61B 18/00*    (2006.01)
(Continued)

(52) U.S. Cl.
CPC .......... *A61B 18/14* (2013.01); *A61B 18/1206* (2013.01); *A61B 18/1402* (2013.01);
(Continued)

(58) Field of Classification Search
CPC .......... A61B 18/14; A61B 2018/00107; C03C 3/00–118
See application file for complete search history.

(56) References Cited

U.S. PATENT DOCUMENTS 3,285,773 A    11/1966    Dunning et al.
3,510,343 A    5/1970    Twells et al.
(Continued)

FOREIGN PATENT DOCUMENTS

CN    101054312    10/2007
DE    102016111390 A1 *    12/2017    ............. C03C 11/00
(Continued)

OTHER PUBLICATIONS

Translation of Foreign Patent Document DE 102016111390 A1 (Year: 2023).*

(Continued)

*Primary Examiner* — Michael F Peffley
*Assistant Examiner* — Nicholas S Borsch
(74) *Attorney, Agent, or Firm* — Husch Blackwell LLP (57) ABSTRACT

A vitreous enamel coating for an electrosurgical metal cutting blade, the coating having a coefficient of thermal expansion substantially near the coefficient of thermal expansion of the metal cutting blade. Selection of materials having similar coefficients of thermal expansion results in an electrosurgical cutting blade with an improved insulating layer, substantially improved durability, or both.

19 Claims, 8 Drawing Sheets

(51) Int. Cl.
*A61B 18/12* (2006.01)
*A61L 31/02* (2006.01)
*A61L 31/14* (2006.01)
*C03C 3/064* (2006.01)
*C03C 3/066* (2006.01)
*C03C 3/091* (2006.01)
*C03C 3/093* (2006.01)
*C03C 4/02* (2006.01)
*C03C 4/16* (2006.01)
*C03C 8/02* (2006.01)
*C03C 8/04* (2006.01)
*C03C 8/14* (2006.01)
*C03C 8/16* (2006.01)
*C03C 10/00* (2006.01)

(52) U.S. Cl.
CPC .......... *A61B 18/148* (2013.01); *A61L 31/026* (2013.01); *A61L 31/14* (2013.01); *C03C 3/064* (2013.01); *C03C 3/066* (2013.01); *C03C 3/091* (2013.01); *C03C 3/093* (2013.01); *C03C 4/02* (2013.01); *C03C 4/16* (2013.01); *C03C 8/02* (2013.01); *C03C 8/04* (2013.01); *C03C 8/14* (2013.01); *C03C 8/16* (2013.01); *C03C 10/00* (2013.01); *C03C 10/0036* (2013.01); *C03C 10/0054* (2013.01); *A61B 2018/00083* (2013.01); *A61B 2018/00107* (2013.01); *A61B 2018/00125* (2013.01); *A61B 2018/00148* (2013.01); *A61B 2018/00601* (2013.01); *A61B 2018/00607* (2013.01); *A61B 2018/1253* (2013.01); *A61B 2018/126* (2013.01); *A61B 2018/1412* (2013.01); *A61B 2018/1415* (2013.01); *C03C 2204/00* (2013.01)

(56) References Cited

U.S. PATENT DOCUMENTS

| | | | |
|---|---|---|---|
| 4,582,056 A | 4/1986 | McCorkle et al. | |
| 4,732,794 A * | 3/1988 | Hyde | C03C 8/02 428/210 |
| 4,820,545 A | 4/1989 | Negrych | |
| 5,393,714 A | 2/1995 | Thometzek et al. | |
| 5,423,806 A | 6/1995 | Dale et al. | |
| 5,573,529 A | 11/1996 | Haak et al. | |
| 5,776,613 A | 7/1998 | Shimatani et al. | |
| 5,779,715 A | 7/1998 | Tu | |
| 5,980,515 A | 11/1999 | Tu | |
| 6,033,402 A | 3/2000 | Tu et al. | |
| 6,071,283 A | 6/2000 | Nardella et al. | |
| 6,080,152 A | 6/2000 | Nardella et al. | |
| 6,135,998 A | 10/2000 | Palanker | |
| 6,183,469 B1 | 2/2001 | Thapliyal et al. | |
| 6,241,692 B1 | 6/2001 | Tu et al. | |
| 6,379,351 B1 | 4/2002 | Thapliyal et al. | |
| 6,419,674 B1 | 7/2002 | Bowser et al. | |
| 6,569,510 B1 * | 5/2003 | Menon | B32B 15/18 428/156 |
| 6,616,744 B1 | 9/2003 | Sainz et al. | |
| 6,623,437 B2 | 9/2003 | Hinchliffe et al. | |
| 6,712,817 B1 | 3/2004 | Goto et al. | |
| 7,107,105 B2 | 9/2006 | Bjorklund et al. | |
| 8,128,636 B2 | 3/2012 | Lui et al. | |
| 8,192,430 B2 | 6/2012 | Goode et al. | |
| 8,428,747 B2 | 4/2013 | Coe et al. | |
| 8,439,910 B2 | 5/2013 | Greep et al. | |
| 8,480,696 B2 | 7/2013 | Clague et al. | |
| 8,632,558 B2 | 1/2014 | Chin et al. | |
| 9,023,040 B2 | 5/2015 | Bloom et al. | |
| 9,028,520 B2 | 5/2015 | Taylor et al. | |
| 9,149,290 B2 | 10/2015 | Goode et al. | |
| 9,155,878 B2 | 10/2015 | Goode et al. | |
| 2003/0129329 A1 * | 7/2003 | Grossman | C03C 8/02 501/6 |
| 2004/0087939 A1 * | 5/2004 | Eggers | A61N 1/05 606/41 |
| 2004/0151745 A1 * | 8/2004 | Zimmer | C03C 14/004 424/401 |
| 2005/0149096 A1 | 7/2005 | Hilal et al. | |
| 2007/0005057 A1 * | 1/2007 | Heim | A61B 18/1402 606/49 |
| 2008/0027428 A1 | 1/2008 | Palanker et al. | |
| 2008/0108443 A1 * | 5/2008 | Jinno | A61B 34/71 464/69 |
| 2010/0009203 A1 * | 1/2010 | Nageno | C03C 8/04 428/428 |
| 2010/0129726 A1 | 5/2010 | Tanida et al. | |
| 2010/0198229 A1 | 8/2010 | Olomutzki et al. | |
| 2010/0222787 A1 | 9/2010 | Goode et al. | |
| 2012/0171420 A1 | 7/2012 | Molins et al. | |
| 2012/0191084 A1 | 7/2012 | Davison et al. | |
| 2012/0282407 A1 | 11/2012 | Singh et al. | |
| 2013/0065250 A1 | 3/2013 | Hubbard et al. | |
| 2013/0183489 A1 | 7/2013 | Cremer et al. | |
| 2013/0226176 A1 | 8/2013 | Kuehner et al. | |
| 2014/0031800 A1 | 1/2014 | Ben et al. | |
| 2014/0276696 A1 | 9/2014 | Schneider | |
| 2014/0276770 A1 | 9/2014 | Ellman | |
| 2014/0276926 A1 | 9/2014 | Hendrick | |
| 2014/0296897 A1 | 10/2014 | Sotak et al. | |
| 2015/0031524 A1 | 1/2015 | Takayama | |
| 2016/0022302 A1 | 1/2016 | Olomutzki et al. | |
| 2016/0175060 A1 * | 6/2016 | Park | A61B 17/00 606/130 |
| 2016/0225966 A1 * | 8/2016 | Maloney | C03C 8/14 |
| 2018/0028258 A1 | 2/2018 | Zamarripa et al. | |
| 2019/0112225 A1 | 4/2019 | Mix et al. | |
| 2019/0185370 A1 | 6/2019 | Cheng et al. | |
| 2019/0192213 A1 | 6/2019 | Cheng et al. | |

FOREIGN PATENT DOCUMENTS

| | | |
|---|---|---|
| EP | 1903957 B1 | 12/2011 |
| ES | 2350943 T3 | 1/2011 |
| GB | 1465372 A | 2/1977 |
| WO | WO-2009046002 A1 | 4/2009 |

OTHER PUBLICATIONS

Borosilicate Glass, Aug. 15, 2011 (Year: 2011).*
Borosilicate Glass Proof of Date (Year: 2023).*
Borosilicate Material Properties, Nov. 18, 2009 (Year: 2009).*
Borosilicate Material Properties Proof of Date (Year: 2023).*
Linear Expansion Coefficients (Year: 2010).*
Linear Expansion Coefficients proof of Date (Year: 2023).*
Peter Hidnert, Thermal Expansion of Titanium, Feb. 1943 (Year: 1943).*
Atlas_Steels_Proof_of_Date (Year: 2023).*
Christopher Brace, Radiofrequency and microwave ablation of the liver, lung, kidney and bone: what are the differences, 2009 (Year: 2009).*
Atlas Steels Grade Data Sheet 630 (17-4PH), Jaunuary 2008, Atlas Steels, (Year: 2008).*
Extended European Search Report for European Application No. EP17869561.5, mailed on Apr. 3, 2020, 6 pages.
International Preliminary Report on Patentability for Application No. PCT/US2017/061615, mailed on May 23, 2019, 8 pages.
International Preliminary Report on Patentability for Application No. PCT/US2017/061623, mailed on May 23, 2019, 9 pages.
International Preliminary Report on Patentability for Application No. PCT/US2017/061626, mailed on May 23, 2019, 7 pages.
International Search Report and Written Opinion for Application No. PCT/US2017/061615, mailed on Feb. 6, 2018, 11 pages.
International Search Report and Written Opinion for Application No. PCT/US2017/061623, mailed on Jan. 29, 2018, 10 pages.
International Search Report and Written Opinion for Application No. PCT/US2017/061626, mailed on Mar. 8, 2018, 9 pages.

(56) References Cited

OTHER PUBLICATIONS

Neuzil P., et al., "Pacemaker and ICD Lead Extraction with Electrosurgical Dissection Sheaths and Standard Transvenous Extraction Systems: Results of a Randomized Trial," EP Europace, vol. 9, Issue—2, Feb. 2007, pp. 98-104.
Okamoto Y., et al., "Extraction of Recalled Riata Leads," The Journal of Innovations in Cardiac Rhythm Management, Jul. 4, 2013, pp. 1305-1314.
Perfecta, "Electrosurgical Dissection System," Cook Vascular Incorporated, Jan. 2013, pp. 1-144.
U.S. Appl. No. 16/327,210, filed Feb. 21, 2019.
U.S. Appl. No. 16/327,215, filed Feb. 21, 2019.
U.S. Appl. No. 15/662,450, filed Jul. 28, 2017.
Gloss Testing Equipment Angle Selection; https://www.linshangtech.com/tech/tech489.html; Oct. 15, 2019 (Year: 2019).
Gloss and Sheen (and drywall finishing levels required ); Master Painters Institute; http://www.paintinfo.com/mpi/approvesheen.shtml; Apr. 2, 2021 (Year: 2021).
Ceramic Technology, Jiaju Li et al., p. 225, China Light Industry Press, Jun. 2006, edition 1. No English translation available.
Civil Engineering Materials, Xinquan Ni et al., p. 281, Wuhan University Press. Jan. 2014. edition 1, No English translation available.
Civil Engineering Materials, Yamei Zhang et al., p. 279, Southeast University Press, Jan. 2013, edition 4, No English translation available.
Britannica Online Enciclopedia : https://www.britannica.com/ , corundum, hemalite, olivine, pyrochlore, nutile, spinal, gamet Nov. 3, 2021 (Year: 2021).
"ASM standard gloss levels", 2020 (Year: 2020), 1 pg.
Ceramic Technology, Jiaju Li et al., p. 225, China Light Industry Press, Jun. 2006, edition 1. No English translation available. Concise statement of relevance included in concurrently filed Supplemental Information Disclosure Statement transmittal.
Civil Engineering Materials, Xiuquan Ni et al., p. 281, Wuhan University Press, Jan. 2014, edition 1 No English translation available. Concise statement of relevance included in concurrently filed Supplmental Information Disclosure Statement transmittal.
Civil Engineering Materials, Yamei Zhang et al., p. 279, Southeast University Press, Jan. 2013, edition 4. No English translation available. Concise statement of relevance included in concurrently filed Supplemental Information Disclosure Statement transmittal.
Office Action from related EP Application No. 17808685.6, dated Oct. 4, 2022, 4 pgs.

\* cited by examiner

CONTROLLED COEFFICIENT OF THERMAL EXPANSION VITREOUS ENAMEL COMPOSITION FOR ELECTROSURGICAL TOOL

CROSS-REFERENCE TO RELATED APPLICATIONS

This application is a National Phase entry of International Application Serial Number PCT/US2017/061615 filed Nov. 14, 2017 and entitled "CONTROLLED COEFFICIENT OF THERMAL EXPANSION VITREOUS ENAMEL COMPOSITION FOR ELECTROSURGICAL TOOL", which claims the benefit of U.S. Provisional Application Ser. No. 62/421,895 filed Nov. 14, 2016 and entitled "ENAMEL COMPOSITION FOR ELECTROSURGICAL TOOL", the disclosures of which are incorporated herein by reference in their entireties.

FIELD OF THE INVENTION

This invention relates to vitreous enamel compositions for coating electrosurgical cutting blades, and to the coated blades and methods for their manufacture and use.

BACKGROUND

Certain electrosurgical cutting equipment utilizes plasma energy to dissect tissue and coagulate blood vessels while producing minimal collateral damage to surrounding tissue. The cutting blade designed for the electrosurgical application often employs an insulating layer on a portion of the cutting blade to prevent energy from dispersing onto the bulk surface of the blade. Additionally, the insulating layer typically defines an uninsulated cutting edge (viz., an exposed electrode). The cutting edge, upon the introduction of a certain pattern of radiofrequency (RF) waveform, creates a substantially uniform and focused electrical field that upon contact with the cells in tissue forms a plasma-mediated discharge.

Cutting blades using a conventional vitreous enamel insulating layer are prone to develop defects that can adversely impact their durability and useful service life. For example, at times the insulating layer on cutting blades can be prone to significant melting or glass flow at defects such as pits and porosity upon exposure to the plasma discharge. Additionally, the insulating layer can develop cracks and chipping during the rapid heating and cooling cycle. All of these resulting occurrences are undesirable and detract from the performance of the vitreous enamel-coated cutting blade.

From the foregoing, it will be appreciated that what is needed in the art is an effective vitreous enamel coating on an electrosurgical cutting blade that does not exhibit the undesirable melt/flow, cracks and chipping resulting from use with plasma. Such a vitreous enamel insulating layer is disclosed and claimed herein.

SUMMARY

The substrate-forming cutting blade for an insulated electrosurgical cutting tool may be produced from various metals. Additionally, the geometry of the metal substrate may vary substantially depending on the intended site or type of surgical use. The varying geometry and intricate designs of electrosurgical cutting tools for certain surgical applications can make the coating and formation of a vitreous enamel insulating layer rather difficult.

The operating environment for vitreous enamel-coated electrosurgical cutting blades also involves extreme variations in temperature locally at the cutting edge due to the rapid plasma-mediated discharge. A rapid temperature increase during the plasma discharge is generally followed by a very fast cool down to about room temperature in a matter of a few seconds. Additionally, the thermal cycling of the electrosurgical cutting blade may be frequent due to the demands of a particular procedure. These extremes, including high operating temperatures above 800° C. at cutting edge and extremely fast thermal cycling, impart residual thermal stresses on the vitreous enamel insulating layer. At those extreme temperatures the glass comprising the vitreous enamel coating may reflow potentially rendering the exposed cutting edge unusable. In other occurrences, the cycling of energy results in the expansion and contraction of the dissimilar materials of construction for the metal cutting blade and the vitreous enamel insulating layer. As a result, the cycling may cause the coating to crack, chip or form other defects, especially when the thermal expansion of the coating material does not match with that of the uncoated metal substrate.

The present invention provides in one aspect an article comprising:
(a) an electrosurgical cutting blade comprising a metal electrode having a coefficient of thermal expansion, and
(b) a vitreous enamel coating on at least a portion of the metal electrode, the vitreous enamel coating having a coefficient of thermal expansion within less than ±30% of the metal electrode coefficient of thermal expansion.

The vitreous enamel coating has a coefficient of thermal expansion (CTE) substantially near the CTE of the uncoated metal substrate. The selection of materials having similar CTE values results in an electrosurgical cutting blade with an improved insulating layer and in certain embodiments, substantially improved durability. In some embodiments, the vitreous enamel and metal substrate CTE values are within 20%, 15%, or even 10% of each other. In some embodiments, the CTE values of the vitreous enamel coating and the uncoated metal substrate may range from about 10 to about $12 \times 10^{-6}/°$ C. In preferred embodiments, the vitreous enamel CTE is below that of the uncoated metal substrate, as in such case it appears that crack formation in the vitreous enamel will be less likely. In especially preferred embodiments, the vitreous enamel coating has a slightly lower CTE than that of the metal substrate (e.g., not more than 10% below that of the metal substrate, so as to place the vitreous enamel under compression during use and protect it from tensile failure and the accompanying formation of cracks or fractures. If the vitreous enamel coating CTE is greater than the metal substrate CTE, then it is preferred that the vitreous enamel coating CTE be no more than 10% greater than the metal substrate CTE. In any event, the chosen vitreous enamel CTE value and comparison metal substrate CTE value may vary based on the composition of the metal substrate used to form the cutting blade.

The invention provides in another aspect a vitreous enamel coating derived from the coating and subsequent firing of an aluminoborosilicate glass frit onto the metal substrate. The components of the glass flit are generally selected to achieve a desired coefficient of thermal expansion. In certain embodiments, the components of the glass flit may also be selected to impart a desired softening temperature to the insulating layer. A softening temperature of at least 500° C. may in some circumstances enhance the durability of the glass. By increasing the softening temperature, the glass may withstand higher temperatures without softening, flowing and degrading its dielectric properties. The metal substrate and its glass flit coating can be fired to create a vitreous enamel insulating layer with dielectric properties. In some embodiments, the coating is delivered onto the metal substrate through a slurry which is formed by combining glass flit powders, binder, and solvent. The binder and solvent can be initially burned off in a burn-out process and the coating subsequently fired at elevated temperatures to form the vitreous enamel insulating layer on the metal substrate.

The invention provides in another aspect a vitreous enamel coating comprising a glass formed from glass frit having, as molar percentages: 30-50% $SiO_2$, 0.5-15% $B_2O_3$, 0.5-10% $Al_2O_3$, 5-30% SrO, 5-30% CaO, and 0.5-20% ZnO, wherein the coating has a coefficient of thermal expansion of about $6\times10^{-6}/°$ C. to about $16\times10^{-6}/°$ C. according to ASTM E228 (and more preferably about $10\times10^{-6}/°$ C. to about $12\times10^{-6}/°$ C., and is disposed on a metal electrode for an electrosurgical cutting blade. In another aspect, the vitreous enamel coating may include a ceramic or crystalline phase. The generation of a certain type of crystalline phase in an amorphous glass may increase the CTE of the vitreous enamel coating. Certain crystalline phases such as hardystonite may enhance the overall performance of the vitreous enamel coating.

The invention provides in yet another aspect a method comprising providing a vitreous enamel precursor, applying the vitreous enamel precursor onto at least a portion of a metal electrode having a coefficient of thermal expansion and being suitable for use as an electrosurgical cutting blade, and firing the vitreous enamel precursor to form a vitreous enamel coating having a coefficient of thermal expansion within less than ±30% of the metal electrode coefficient of thermal expansion.

The electrosurgical cutting blade with its vitreous enamel insulating layer may be connected to a power source on an electrosurgical generator. The invention thus provides in another aspect a method comprising intermittently supplying radiofrequency energy to an electrosurgical cutting blade to create a plasma-mediated discharge and thereby heat and cool the blade, wherein the blade comprises a metal electrode having a coefficient of thermal expansion and a vitreous enamel coating on at least a portion of the metal electrode, the vitreous enamel coating having a coefficient of thermal expansion within less than ±30% of the metal electrode coefficient of thermal expansion.

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

The details of one or more embodiments of the invention are set forth in the description below. Other features, objects, and advantages of the invention will be apparent from the description, drawing, and from the claims.

BRIEF DESCRIPTION OF THE DRAWING

In the accompanying Drawing.

Like reference symbols in the various figures of the Drawing indicate like elements. The elements in FIG. 1 and FIG. 3 are not to scale.

Selected Definitions

Unless otherwise specified, the following terms as used herein have the meanings provided below.

As used herein, "a," "an," "the," "at least one," and "one or more" are used interchangeably. Thus, for example, a coating composition that comprises "an" additive can be interpreted to mean that the coating composition includes "one or more" additives.

The term "amorphous" means a solid composition that lacks the order present in crystalline structures.

The terms "coefficient of thermal expansion" or "CTE" describes a thermomechanical property of a material and its ability to expand in size as the temperature is raised. For purposes of this disclosure, the CTE value is measured in accordance with ASTM E228-17, Standard Test Method for Linear Thermal Expansion of Solid Materials with a Push-Rod Dilatometer. The test heating rate is 5° C./min and the temperature range is from room temperature to about 1000° C. Those of ordinary skill in the art will recognize that the vitreous enamel is not tested after it is coated onto the metal electrode but rather the fired glass frit comprising the vitreous enamel is tested and corresponds to the CTE value of the vitreous enamel after coating and firing.

The term "crystalline" refers to a solid material that possesses a highly ordered or arranged structure, and may in some circumstances form a crystal lattice.

The terms "electrosurgical cutting tool" or "electrosurgical cutting blade" generally refer to the electrosurgical equipment use of plasma energy to dissect tissue or coagulate blood vessels while producing minimal collateral damage to surrounding tissue.

The terms "enamel" or "vitreous enamel" describe a transparent, semitransparent or opaque glassy substance applied to metallic or other hard surfaces, and capable of serving as a dielectric or insulating layer for an electrosurgical cutting blade.

The term "glass-ceramic" refers to a vitreous enamel composition that includes both an amorphous phase and a crystalline phase.

The term "glass frit" means the basic materials, often in particulate form, that may be wholly fused, for making glass or vitreous enamel.

The term "metal substrate" refers the metal electrode of an electrosurgical cutting tool that forms the cutting blade and provides a base upon which the vitreous enamel is applied.

The term "opaque" refers to a glass that reflects rather than refracts light in a wavelength range of interest (typically but not in all cases the visible light range from 400 to 700 nm).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The recitation of numerical ranges by endpoints includes all numbers subsumed within that range (e.g., 1 to 5 includes 1, 1.5, 2, 2.75, 3, 3.80, 4, 5, etc.). Furthermore, disclosure of a range includes disclosure of all subranges included within the broader range (e.g., 1 to 5 discloses 1 to 4, 1.5 to 4.5, 1 to 2, etc.).

DETAILED DESCRIPTION

Figure 1:
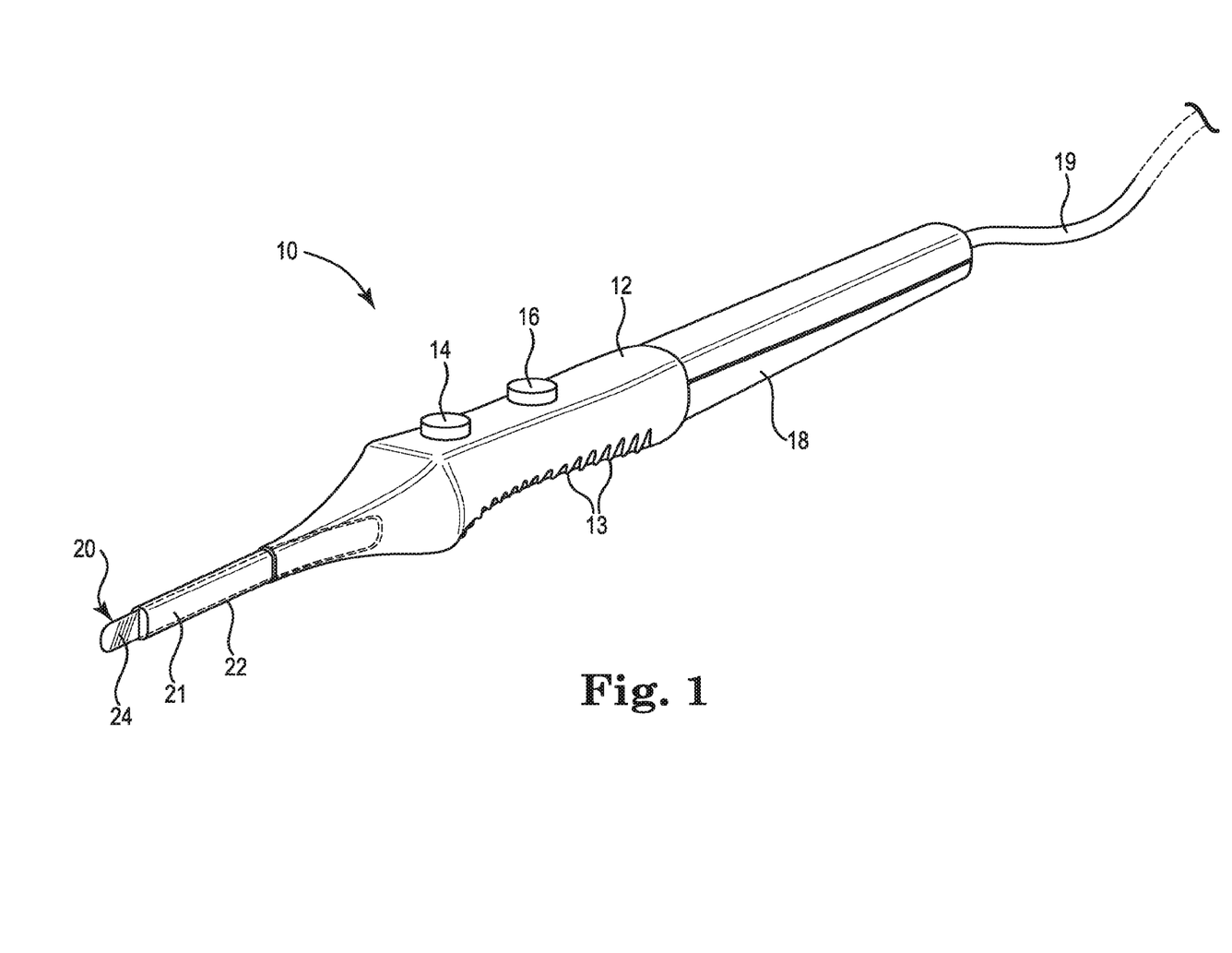
FIG. 1 is a perspective view of an electrosurgical cutting tool.

FIG. 1 depicts an embodiment of an electrosurgical cutting device 10. Device 10 includes an insulated handle 12 with hand (e.g., finger) grip ridges 13 as shown on the lower part thereof. This portion is intended to be held in the surgeon's hand (not shown in FIG. 1). Two control buttons 14, 16 activate electric switches (not shown in FIG. 1) which are provided for respectively selecting cutting or coagulation regimes. The rear portion 18 is for balance and for housing at least one cable 19 that may terminate in a conventional electrical connector (not shown in FIG. 1) for connection to a lead, leads or mating connector of a radiofrequency energy power supply (not shown in FIG. 1). The dimensions of the device of FIG. 1 are such that it is comfortably held in a hand, yet small enough for surgery for the intended application. The working end of the device of FIG. 1 includes at its distal end an electrosurgical cutting blade 20. Electrosurgical cutting blade 20 includes a metal substrate or electrode 21 housed in an intermediate portion or shaft 22. Intermediate portion 22 provides an insulated support that holds and extends the distal end of electrosurgical cutting blade 20 at an appropriate surgical viewing and cutting or coagulating distance from the surgeon's hand. The exposed distal portion of electrosurgical cutting blade 20 includes a vitreous enamel insulative coating 24. A non-limiting embodiment of an exemplary electrosurgical device is disclosed in U.S. Pat. No. 8,414,572 B2, herein incorporated by reference in its entirety.

As depicted in FIG. 1, device 10 has a single, flattened blade 20 fixedly mounted in intermediate portion 22. As will be appreciated by persons having ordinary skill in the art, the disclosed electrosurgical device may have a variety of other blade shapes and blade configurations, including blades with square edged, slant-edged, cylindrical, needle-like, bent, bendable or telescoping features. The disclosed electrosurgical device may be a monopolar device such as is shown in FIG. 1, or a bipolar device with two or more electrodes as may be used in some forms of electrosurgery.

In operation, the steps involved for cutting or otherwise operating on (e.g., coagulating) tissue with an electrosurgical device such as device 10 of FIG. 1 generally include contacting the tissue with a plasma generating electrode and applying an electric signal, having in some cases a low duty-cycle RF waveform, to the electrode. The signal causes the formation of a plasma discharge along the electrode between the electrode edge and the tissue and this plasma performs the tissue cutting or other operation.

The actual nature of the applied electrical signals which are suitable to create the desired plasma effect is well known in the field. For instance, in one embodiment the applied signal is an RF signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval therebetween of 0.1 to 10 microseconds. The actual pulses are typically square waves and bi-phasic, that is alternating positive and negative amplitudes. Generally the interval between pulses must be shorter than a lifetime of the plasma vapor cavity in order to maintain the cavity and the plasma regime during each pulse burst. In one embodiment the bursts are separated by a duration of at least one millisecond.

Figure 2:
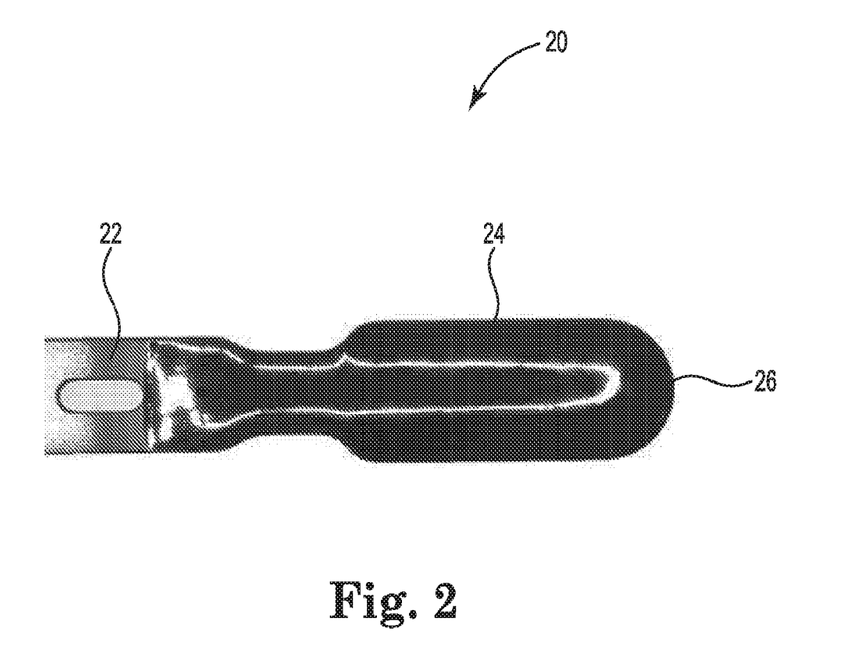
FIG. 2 is an orthogonal side view of a vitreous enamel-coated electrosurgical cutting blade.

The energy is delivered to the functional edge of the device through an electrosurgical cutting blade. FIG. 2 is an orthogonal side view of one embodiment of an electrosurgical cutting blade 20. The electrosurgical cutting blade 20 includes a metal electrode or substrate 22 at least a portion of which is coated with a vitreous enamel coating 24. An exposed edge 26 of the metal substrate 22, upon the introduction of radiofrequency energy, is capable of creating a substantially uniform and enhanced electrical field that upon contact with the cells in tissue forms the plasma medium. The vitreous enamel coating 24 functions as a non-conductive surface and thereby limits the formation of the plasma medium to the defined edge 26.

Figure 3:
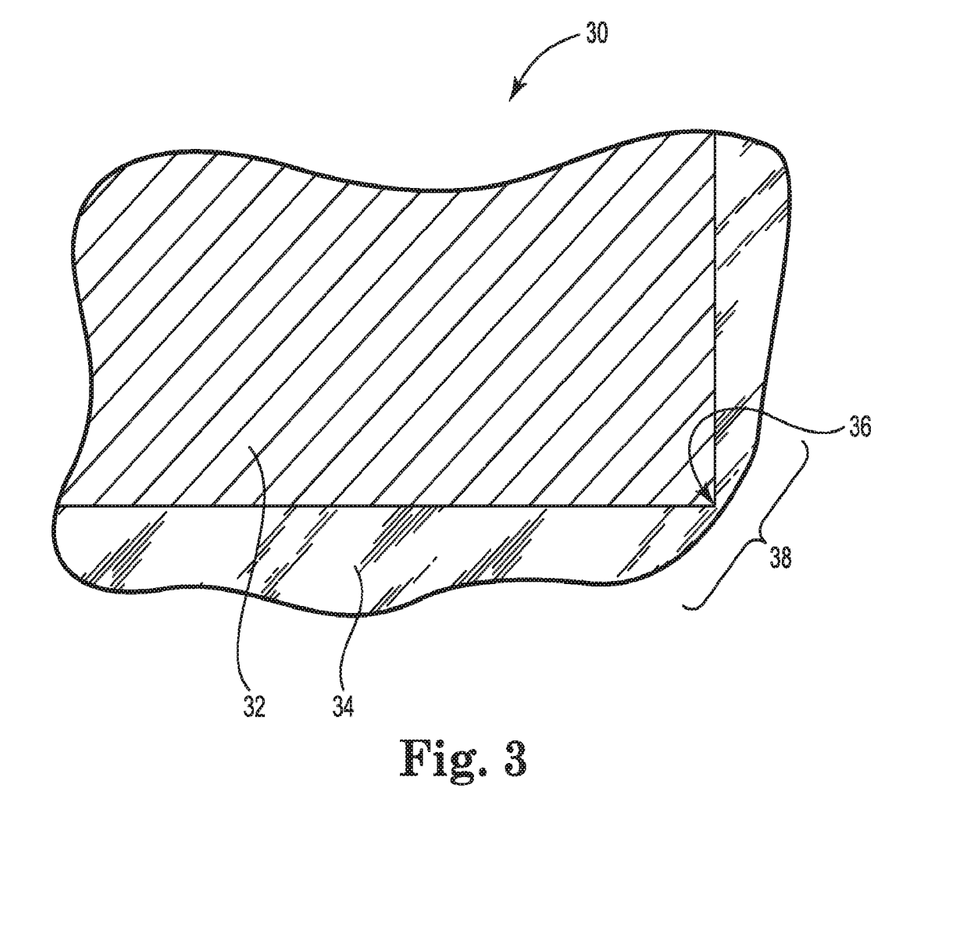
FIG. 3 is a cross-sectional schematic view of an edge portion of a vitreous enamel-coated electrosurgical cutting blade.

FIG. 3 is a cross-sectional schematic view of an edge portion 38 of a vitreous enamel-coated electrosurgical cutting blade 30. Blade 30 includes metal electrode substrate 32, vitreous enamel coating 34, and edge 36. Due to surface tension and other factors during application or firing of the frit from which coating 34 is made, coating 34 typically will have a reduced thickness near edge 36. In some embodiments, edge 36 may be exposed following firing. If desired, a mechanical impact, abrasive, electrical energy, acid etching or other measures may be used to remove a portion of, or to discourage the formation of, coating 34 proximate edge 36, thereby resulting in a region with reduced thickness or no coating at all proximate edge 36. Such reduced thickness or exposed edge provides a localized reduction in the breakdown voltage of coating 36 and helps promotes initial plasma formation and plasma maintenance proximate edge 36 when electromagnetic energy is applied to metal electrode 32.

Figure 4:
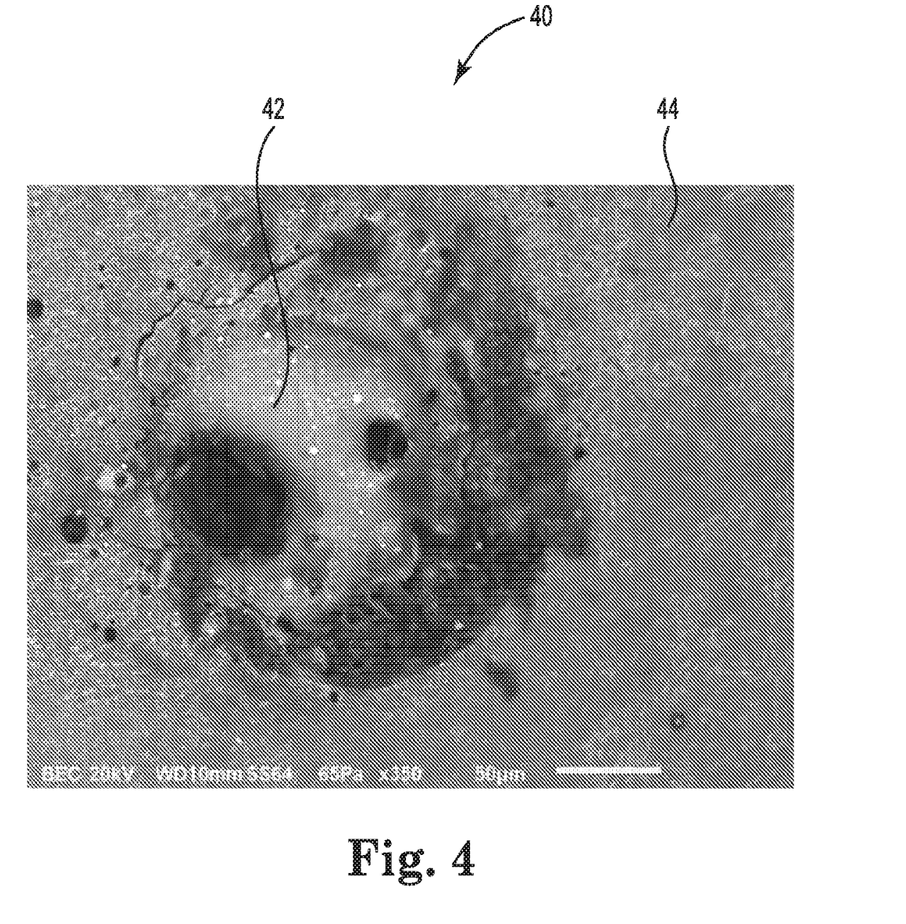
FIG. 4 is a photomicrograph of an electrosurgical cutting blade illustrating one form of a defect.

The harsh operating environment of high temperature and the exceedingly fast thermal cycling of the cutting edge can create an extreme environment for conventional enamel coatings. Certain embodiments of conventional vitreous enamels can exhibit defects. FIG. 4 depicts one such defect referred to as glass reflow. The extreme thermal environment arising during electrosurgery can cause conventional vitreous enamel to at least flow and partially melt. FIG. 4 is a photomicrograph of a portion of an electrosurgical cutting blade 40 that exhibits a reflow defect 42 in vitreous enamel coating 44.

Figure 5:
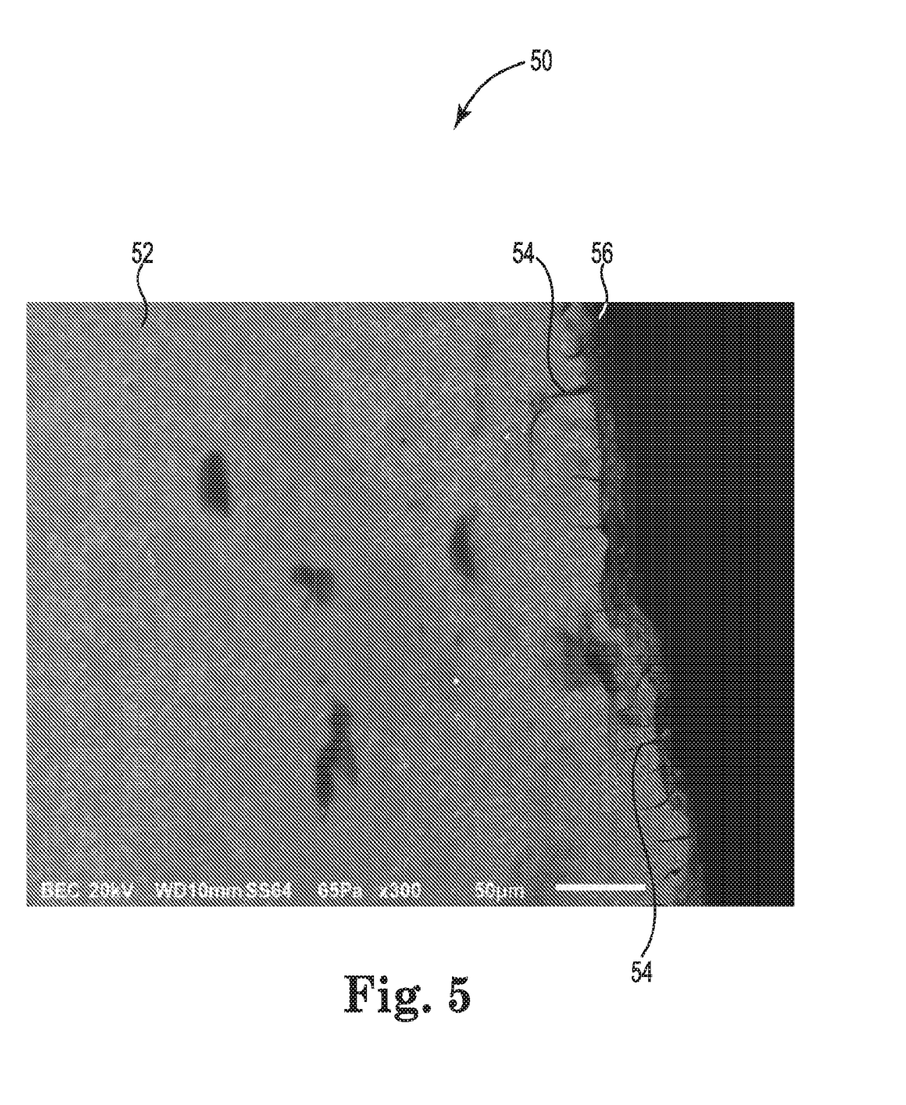
FIG. 5 is a photomicrograph of an electrosurgical cutting blade illustrating another form of a defect.

Without being bound by theory, it is believed that incompatible thermomechanical properties of the vitreous enamel and the metal substrate may promote or otherwise impact the formation of defects in a conventional vitreous enamel. For example, FIG. 5 is a photomicrograph of a portion of an electrosurgical cutting blade 50. The conventional vitreous enamel 52 of electrosurgical cutting blade 50 shows cracks 54 at the cutting edge 56 of cutting blade 50.

Figure 6:
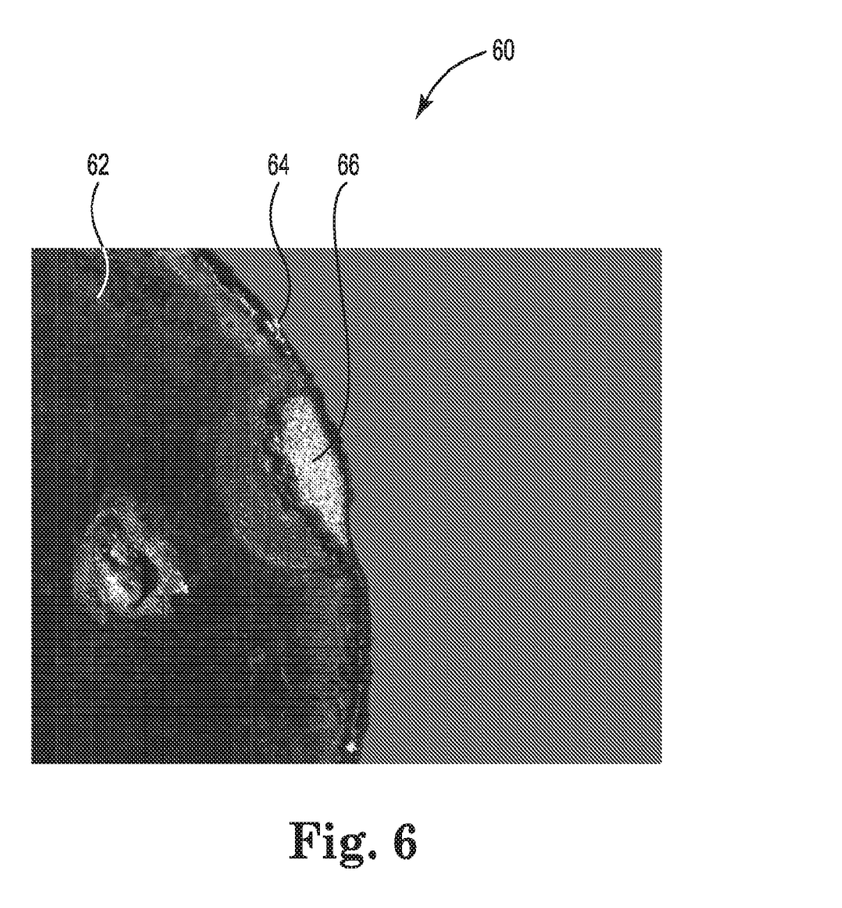
FIG. 6 is a photomicrograph of an electrosurgical cutting blade illustrating yet another form of a defect.

FIG. 6 is a photomicrograph showing another example of a defect in conventional enamel coatings on electrosurgical cutting blades. FIG. 6 depicts an electrosurgical cutting blade 60 having a vitreous enamel coating 62. The edge 64 of the electrosurgical cutting blade 60 has a chip 66 that developed during use. It is believed that the mismatch in thermomechanical properties, such as the coefficient of thermal expansion, can create defects in the vitreous enamel coating during thermal cycling. The deleterious impact of a mismatch in thermomechanical properties on the coating may be amplified due to the exceedingly fast heating and cooling at an extreme temperature differential during use of the electrosurgical tool.

Figure 7:
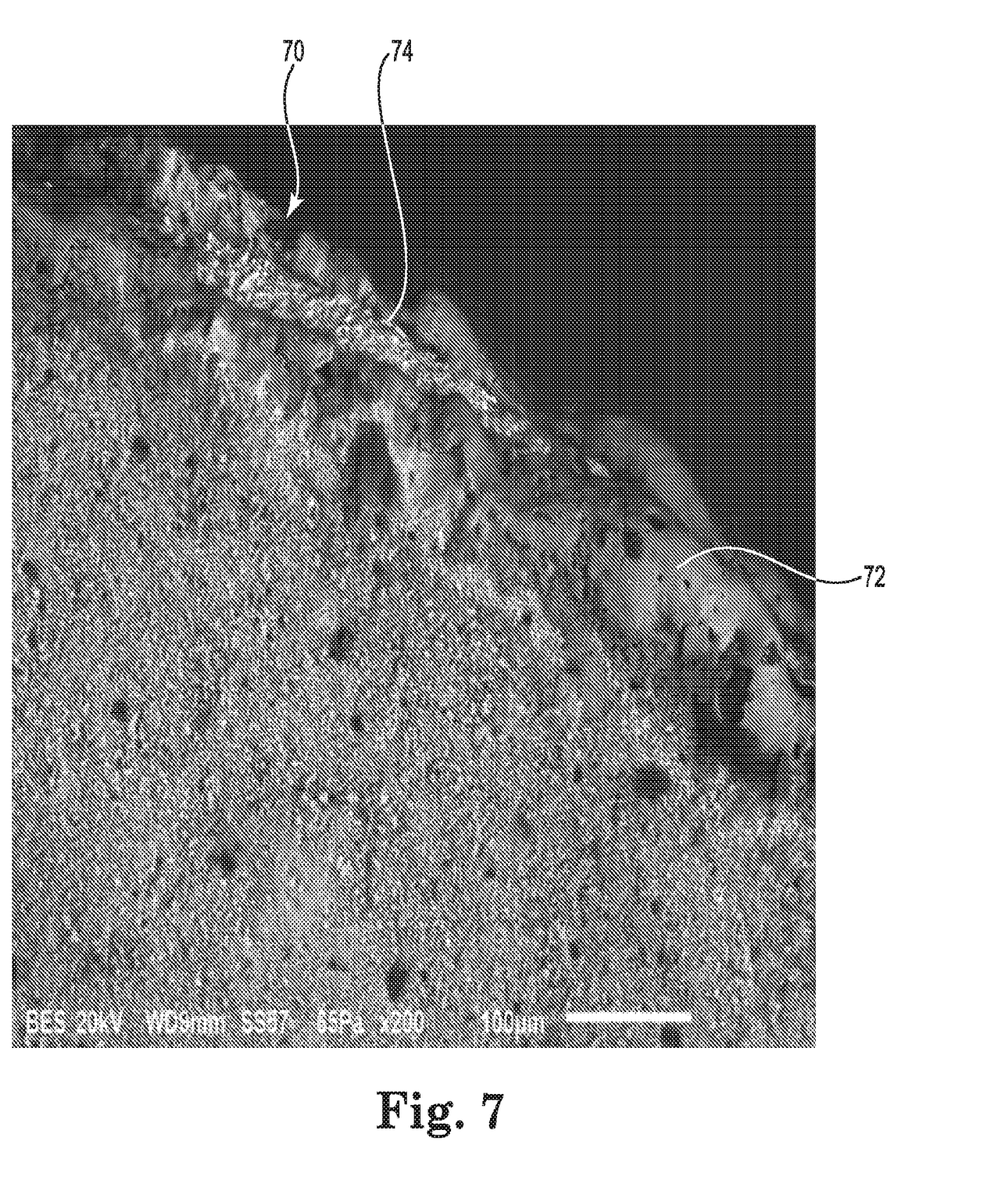
FIG. 7 is a photomicrograph of the Example 1 electrosurgical cutting blade after 20 minutes of use.

FIG. 7 depicts an electrosurgical cutting blade of the invention 70 as described in Example 1, after 20 minutes of use on porcine tissue. Vitreous enamel coating 72 and edge 74 are free of visible cracks like the cracks 54 shown in FIG. 5, and are free of chips like chip 66 shown in FIG. 6. The vitreous enamel coating 72 possesses thermomechanical properties substantially similar to those of the metal substrate used to form cutting blade 70. The creation of a vitreous enamel coating on the metal substrate with similar thermomechanical properties, such as the coefficient of thermal expansion or CTE, results in a durable coating that is far better suited to withstand extreme operating environments associated with the formation of plasma for surgical purposes.

The disclosed electrosurgical cutting blade includes a metal electrode that provides electrical connectivity to the power source and offers (or may be altered to offer) an exposed edge to enable the formation of plasma. Non-limiting examples of metals suitable to form electrodes include titanium, tantalum, molybdenum, tungsten, stainless steel, or alloys thereof. In some embodiments, the metal electrode can be cut or stamped from metal substrates. Secondary process steps such as etching, grinding or polishing may also be used on blades intended for use in certain surgical applications. The dimensions and shape of the metal electrode may also vary to accommodate different surgical applications. The metal electrode in some preferred embodiments possesses a CTE value from about 6, 8 or $10 \times 10^{-6}/°$C. up to about 11, 12, or $16 \times 10^{-6}/$C.

The vitreous enamel may comprise any suitable glass composition or glass-ceramic composition that is substantially near the CTE value of the selected metal electrode. The selection of glass or glass-ceramic materials will depend on several factors including, but not limited to, the end use surgical application, blade design, expected temperatures during plasma formation, power voltage of the RF generator, water content of the tissue, and nature and extent of bonding to the metal substrate. In certain aspects, the glass or glass-ceramic composition may be selected to achieve a softening temperature that is near or preferably above the temperatures realized during plasma formation. For example, the softening temperature of a glass or glass-ceramic composition may be at least 500° C., at least 600° C. or at least 700° C.

In certain aspects, the vitreous enamel composition may be an amorphous glass. In other embodiments, the vitreous enamel may include a glass-ceramic composition. Glass-ceramic compositions may possess a crystalline phase along with the amorphous glass. The crystallinity of the vitreous enamel upon firing and formation may beneficially enhance the CTE of the vitreous enamel. Those of ordinary skill in the art with knowledge of this disclosure will recognize that the vitreous enamel may be selectively designed to generate a CTE value close to the desired metal substrate. Non-limiting examples of crystalline phases include $Ca_2ZnSi_2O_7$ (hardystonite) or $Sr_2SiO_4$. Other combinations of compounds, such as nucleating agents, may be included in a glass frit and fired to create a glass-ceramic composition with at least a partial crystallinity that beneficially impacts the thermomechanical properties of the vitreous enamel-coated electrosurgical cutting blade.

The vitreous enamel may be created through the combination of various compounds to form certain types of glass. One embodiment includes the formation of an aluminoborosilicate glass with at least $SiO_2$, $B_2O_3$ and $Al_2O_3$ compounds. In a preferred aluminoborosilicate glass embodiment, the glass frit includes one or more alkaline earth oxides, as such oxides may increase the CTE of an aluminoborosilicate glass. Preferred such alkaline earth oxides include magnesium oxide (MgO), calcium oxide (CaO), strontium oxide (SrO) and barium oxide (BaO). Higher molecular weight alkaline earth oxides tend to provide higher CTE values, and thus on that basis BaO may be preferred. However, BaO may also tend to react with chromium in a stainless steel substrate to produce a thin intermediate layer having a significantly higher CTE than that of the substrate or the vitreous enamel coating. Consequently SrO is an especially preferred alkaline earth oxide for use in the disclosed aluminoborosilicate glasses.

The chosen glass compositions may include other compounds to impart or enhance certain features or characteristics such as glass transition temperature, nucleation, opacity, water resistance, crystallinity, color, diffuse reflection characteristics, CTE and dielectric properties. For example, the glass may include colored pigments as described in copending Application Serial No. PCT/US2017/061623 filed Nov. 14, 2017, or ingredients to reduce specular reflection characteristics and increase diffuse reflection characteristics as described in copending Application Serial No. PCT/US2017/061626 filed Nov. 14, 2017. Exemplary and non-limiting examples of other compounds that may be components of a glass frit to form the vitreous enamel include the alkaline earth oxides mentioned above, zinc oxide, magnesium oxide, sodium oxide, and potassium oxide. Such compounds may optionally be included in the glass frit at molar percentages ranging on a molar percentage from a trace, 0.1%, 1%, 2%, 5% or 10% up to about 5%, 10%, 15% 20%, 30% or 40%. The frit desirably excludes materials that would not be biocompatible, for example lead or other toxic metals and their oxides. Exemplary glass frits and glasses include those from suppliers such as Elan Technology, Ferro Corporation, Mo-Sci Corporation and Schott AG. In a preferred embodiment, a glass frit having the following compounds and molar percentages may be well suited for forming a vitreous enamel on an electrosurgical cutting blade: $SiO_2$ 30-50%, $B_2O_3$ 0.5-15%, $Al_2O_3$ 0.5-10%, SrO 5-30%, CaO 5-30%, and ZnO 0.5-20%.

Without being bound by theory, it is believed that the components in the disclosed vitreous enamel flit and vitreous enamel coating offer various attributes. For example, the function of each component in the glass composition may provide or offer certain features to the resulting enamel. The $Si_2O$ helps form the glass network. Modifiers such as alkali and alkaline earth oxides may increase the CTE value and potentially decrease the glass transition temperature. $Al_2O_3$ may modify the crystallization rate. Minor additives such as $TiO_2$ and $ZrO_2$ may act as nucleating agents. $B_2O_3$ may modify the extent and rate of crystallization and improve wetting of the glass to the metal substrate. $B_2O_3$ may also increase the vitreous enamel CTE. High CTE partially crystallizing systems may for example also include one or both of SrO and BaO.

Figure 8:
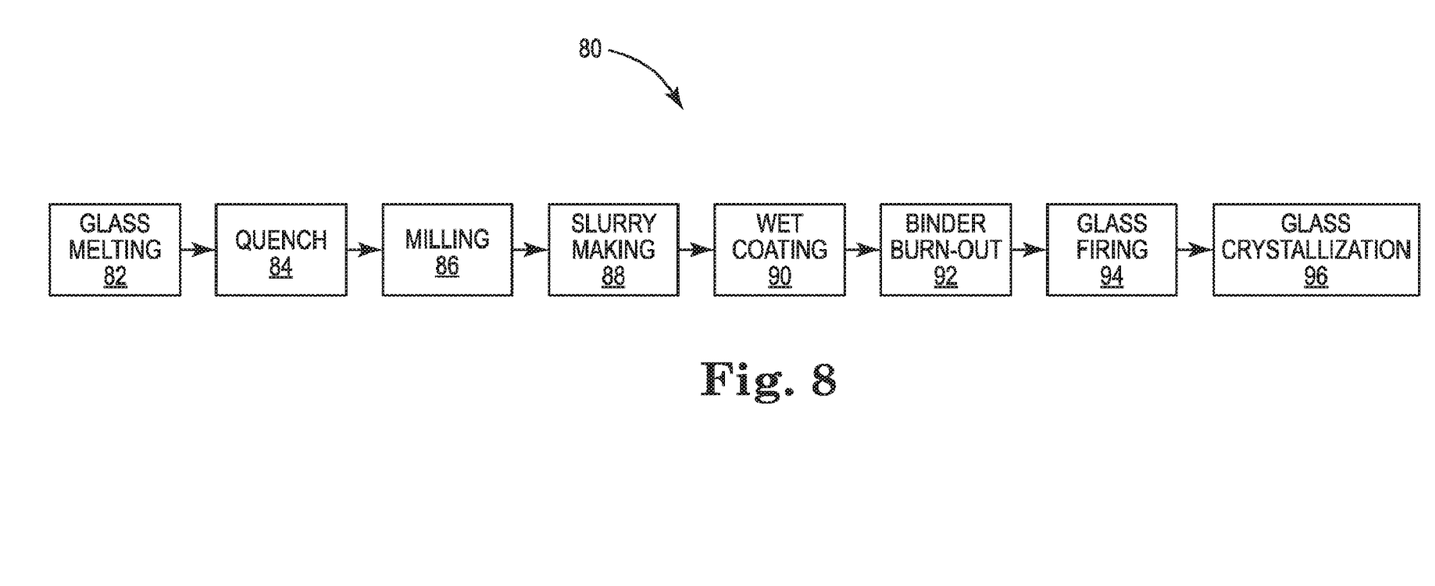
FIG. 8 is a schematic of one embodiment of a process for forming a vitreous enamel coating on an electrosurgical cutting blade.

FIG. 8 is an illustration of one embodiment of a process 80 suitable for forming a vitreous enamel coating on an electrosurgical cutting blade from a glass flit. The frit may be separately-supplied or may be manually prepared just prior to use. Glass melting step 82 is typically performed by mixing and melting the fit components in a furnace and quenching 84 the melt to form a solidified glass material. The resulting glass material is then milled 86 to a desired particle size that will support coating and formation of a vitreous enamel on the metal substrate. Those of ordinary skill in the art will recognize that particle size may have an impact on the properties of the resulting vitreous enamel. In certain embodiments, the particles may have a $d_{90}$ value between about 20 and about 50 µm (viz., 90 vol. % of the particles may in such embodiments have an average diameter below about 20 to below about 50 µm). In an optional wet coating step, a slurry 88 is prepared to facilitate the coating 90 of glass powder onto the metal substrate. The slurry may for example be prepared by dispersing the glass particles in a binder and carrier. The carrier can be any suitable solvent that is capable of maintaining a stable dispersion and a suitable viscosity for coating. Non-limiting examples of suitable carriers include mineral oil, ethanol, terpineol or combinations thereof. The binder enhances wet out and coating of the metal substrate during the coating process. Non-limiting examples of suitable binders include polyvinyl butyral, polyvinyl alcohol, and ethyl cellulose. Alternatively, the coating may be applied using a dry coating process, thereby alleviating the need for slurry formation. In any event, a variety of coating processes 90 may be employed. Non-limiting examples include electrophoretic deposition, dip coating, roll coating, spray coating or other similar application processes. The coating is preferably applied at a thickness sufficient to obtain a vitreous enamel coating that, after firing, will not unduly degrade during plasma formation and preferably will not suffer the defects that arise when using conventional vitreous enamel coatings. In a preferred embodiment, the metal substrate is coated to a vitreous achieve enamel coating thickness of about 75 µm to about 100 µm. In certain aspects in wet coating processes, the viscosity of the slurry may be controlled to address the coating thickness. Additionally, the coating is preferably applied in a manner that provides an exposed or only thinly-coated cutting edge. The edge may as discussed in connection with FIG. 3 be manually exposed by removing a portion of the vitreous enamel coating. The selection of a particular coating process may be dependent on various factors, including the metal substrate, the size and geometry of the cutting blade, and the type of glass frit, among others. Those of ordinary skill in the art will be capable of matching a particular coating process to achieve a desired enamel thickness on an electrosurgical cutting blade.

When using the slurry making step 88 and wet coating step 90 shown in FIG. 8, the binder and solvent are typically removed in a binder burn-out step 92. The electrosurgical cutting blade may be heated to a temperature and for a time sufficient to drive off any binder and solvent from the glass powder. The duration and temperature for this process may vary depending on the solvent or binder composition. In some embodiments, the temperature ranges up to about 500° C. for a time up to about 60 minutes. After this process, the remaining coating has green strength and ready for glass firing to form a vitreous enamel.

The glass firing process 94 encompasses ramping up the furnace temperature to the glass's firing temperature for a limited time to form the vitreous enamel, fuse it to the substrate, and anneal the final coating. Optionally, certain embodiments may allow for the formation of a crystalline phase 96. The firing generally takes place above 700° C. and in some embodiments above 750° C., or even above 800° C. The duration of the firing process and the time the coated substrate is held at temperature may for example vary depending upon the glass composition, coating thickness, type of metal substrate, blade shape and size, and other factors. Additionally, the let-down temperature may vary and may be staggered to enable solidification, annealing and stress relief. In certain embodiments, the annealing temperature is established at or above the T, value for the selected vitreous enamel composition. The resulting vitreous enamel-coated electrosurgical cutting blade may for example be very similar in appearance to the embodiment shown in FIG. 2.

The properties and characteristics of the vitreous enamel-coated electrosurgical cutting blades produced according to this disclosure can provide greater durability and extended useful service life compared to blades bearing a conventional vitreous enamel coating. The CTE values of the metal substrate and the vitreous enamel on the disclosed electrosurgical cutting blade are substantially near each other. This feature may result in the elimination of defects in the vitreous enamel of the electrosurgical cutting blade. In some embodiments, the metal substrate CTE value may range from about 6, 8 or $10 \times 10^{-6}/°$ C. up to about 11, 12, or $16 \times 10^{-6}/°$ C. The dielectric strength of the coatings may vary and in preferred embodiments may be greater than about 20.000, about 30,000 or about 40,000 volts/mm (about 508, about 762 or about 1016 volts/mil) as measured using ASTM D149-09. In some embodiments, the durability of the blade may be demonstrated by wearing out the electrosurgical cutting blade at a high voltage electrosurgical generator setting for 20 minutes of representative use in the operating room. The widths of the vitreous enamel-coated electrosurgical blade samples measured after wear are compared to the widths before wear to calculate percent blade width reduction. In some embodiments, the percent blade width reduction varies from about −6% to −11%.

Test Procedures

Coefficient of Thermal Expansion: ASTM E228 (Standard Test Method for Linear Thermal Expansion of Solid Materials with a Push-Rod Dilatometer).

A push-rod dilatometer includes of a cylinder of a material of a known thermal expansion coefficient, surrounded by a heating device. A sample is placed inside and against the end of the cylinder. A rod of the same material as the cylinder is placed against the sample. The other end of the rod is connected to a linear variable differential transformer (LVDT) which measures very small changes in the position of the end of the rod. Heating the region containing the sample results in expansion of the sample, the surrounding cylinder and the rod. If the expansion of the sample has a different thermal expansion coefficient from that of the apparatus, the end of the rod will be displaced by the account determined by the sample length and by the difference in the thermal expansion coefficients between the sample and the apparatus material. The true thermal expansion coefficient of the sample is determined by correcting the displacement versus temperature data for the expansion of the apparatus. Then the thermal expansion coefficient of the sample is obtained by:

$$\text{linear thermal expansion coefficient} = \frac{\Delta L}{L_0} \times \frac{1}{\Delta T}$$

Where $L_0$ is the original length of the sample, $\Delta L$ is the true displacement of the sample (expansion) and $\Delta T$ is the temperature difference over which the displacement happens.

Dielectric Strength: ASTM D149-09 (Standard Test Method for Dielectric Breakdown Voltage and Dielectric Strength of Solid Electrical Insulating Materials at Commercial Power Frequencies).

A test article is prepared by creating a metal coupon dimensioned 1"×1" with a vitreous enamel coating to facilitate testing. A 120-degree point probe is placed on the surface of enamel coating to serve as the positive terminal electrode of the dielectric strength tester, and a negative terminal electrode is connected to the metal coupon. The break-down voltage is measured by applying up to 6000 Volts AC peak to peak at 100 volts/second ramp rate and 60 Hz frequency waveform accepting up to 1 mA leakage current. The break-down voltage is divided by the respective enamel coating thickness under test to obtain the dielectric strength, expressed in volts/mm or in volts/mil.

Durability: Blade Width Reduction Test.

Durability may be demonstrated by wearing out an electrosurgical blade on ex-vivo porcine tissue using high voltage electrosurgical generator settings to simulate a worst case use scenario. For example, a vitreous enamel-coated electrosurgical blade may be manually applied using plasma to porcine tissue to simulate extended (e.g., up to 20 minutes) of representative use in the operating room. The width of the vitreous enamel-coated blade is measured before and after wear. The percent blade width reduction is obtained by:

$$\text{Percent blade width reduction } (\%\ BWR) = \frac{BW_{20} - BW_0}{BW_0} \times 100$$

Where, $BW_0$ is the width of the sample before wear, and $BW_{20}$ is the width of the sample after 20 minutes of wear. Percent blade width reduction is typically a negative value since blade width reduces after wear.

EXAMPLES

Examples 1 and 2

The materials used to make the vitreous enamel-coated electrosurgical blades of Examples 1 and 2 are listed in Table 1. For Examples 1 and 2, the appropriate amounts of solvent, dispersant and glass powders listed in Table 2 were weighed out and mixed together. The mixtures were ball milled for about two hours to ensure an appropriate level of dispersion. The binder was added into the mixture and ball milled for about 4 hours to create a slurry. The viscosity of each slurry was measured using a Brookfield DV2T (LV) viscometer and spindle SC4-18/13R. The viscosity of each slurry was maintained above 1500 cp at 0.2 rpm. Each slurry was applied onto 420 stainless steel electrosurgical cutting blades using a dipping process. After the slurry coating was applied, the coated blades were subjected to burnout at about 600° C. for more than 60 minutes and subsequent firing at a temperature greater than 800° C. for more than 10 minutes. Upon the slow ramp down of the temperature to room temperature, the vitreous enamel-coated electrosurgical blades were visually inspected and analyzed for crystallinity and CTE. The vitreous enamel of Example 1 exhibited sufficient enamel coverage and possessed a CTE value according to ASTM E228 of $10.94 \times 10^{-6}/°$ C. as measured over a temperature range of 25-600° C. X-Ray Diffraction results indicated a $Ca_2SiO_4$ crystalline phase after heat treating. The electrosurgical blade substrate had a CTE value of $11.3 \times 10^{-6}/C°$ as measured over a temperature range of 25-500° C.

TABLE 1

| Materials | |
|---|---|
| Glass 1 | Ba—Ca—Si—B—Al alkaline earth aluminoborosilicate glass |
| Glass 2 | Sr—Si—Ca—Zn—Al—Ti—B alkaline earth aluminoborosilicate glass |
| Binder | ethyl cellulose |
| Solvent | Toluene/ethanol mixture |
| Dispersant | triethyl phosphate |

TABLE 2

| Formulations | | |
|---|---|---|
| Ingredient | Example 1 (wt %) | Example 2 (wt %) |
| Glass 1 | 58 | |
| Glass 2 | | 58 |
| Binder | 23.8 | 23.8 |
| Solvent | 17 | 17 |
| Dispersant | 1.2 | 1.2 |
| | 100 | 100 |

The Example 1 blades were subjected to wear testing on porcine tissue using a PEAK AEX™ electrosurgical generator from Medtronic, using 20 minutes at Cut Mode 7 for a first coated blade and 20 minutes at Coagulation Mode 8 for a second coated blade to evaluate coating durability. The above-mentioned FIG. 7 photomicrograph shows one of the blades after the wear test. Despite the thermal cycling caused by the rapid on-off supply of energy, the vitreous enamel coating did not develop visible cracks or chips. The blades exhibited a blade width reduction of −6.9% under Cut Mode wear and −6.5% under Coagulation Mode wear.

The vitreous enamel of Example 2 exhibited sufficient enamel coverage and possessed a CTE value according to ASTM E228 of $11.7 \times 10^{-6}/C$ as measured over a temperature range of 25-600° C. X-Ray Diffraction results indicated the presence of a crystalline $BaSiO_3$ and $BaAl_2Si_2O_8$ phase. After 20 minutes of use, the vitreous enamel developed small visible cracks but far fewer than conventional vitreous enamel coated cutting blades. The blades exhibited a blade width reduction of −6.4% under Cut Mode wear and −8.8% under Coagulation Mode wear.

Comparison Example 1

In Comparison Example 1, the translucent black, amorphous vitreous enamel coating from a PEAK PLASMABLADE™ 4.0 soft tissue dissection device from Medtronic was analyzed and found to have a CTE of $7.9 \times 10^{-6}/°$ C. as measured over a temperature range of 25–460° C. This value was 69.9% of the CTE for the underlying 420 stainless steel substrate.

Example 3

A glass similar to that used in Example 2 was modified to reduce the glass CTE value and place the coating under greater compression during use, by suppressing the rapid crystallization of hardystonite (by reducing the ZnO content in the frit), improving control of crystallization (by increasing the $Al_2O_3$ content in the frit) and improving wetting and the amount of the glassy phase present (by increasing the $B_2O_3$ content in the fit). Using the method of Examples 1 and 2, the glass was coated onto electrosurgical blades and evaluated to determine its wear resistance. The thus-modified vitreous glass coating had a CTE value of $10.1 \times 10^{-6}/°$ C. as measured over a temperature range of 25-600° C. and improved crack resistance compared to the Example 2 coating. Using six blade samples and performing both 10 minutes of Cut Mode 10 testing followed by 10 minutes of Coagulation Mode 10 testing on each blade, the blades exhibited an average blade width reduction value of −10.9%.

Example 4

Using the method of Examples 1 and 2, the Example 2 glass was modified by the addition of 3 wt. % F6333 black pigment from Ferro, Inc. The resulting vitreous glass coating had an opaque, glossy appearance, and unchanged CTE, Tg and Ts (softening temperature) values.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

The invention claimed is:

1. An article comprising:
    (a) an electrosurgical cutting blade formed as a monopolar device, the electrosurgical cutting blade comprising a metal electrode having a coefficient of thermal expansion and an exposed cutting edge, and
    (b) a solidified vitreous enamel coating on at least a portion of the metal electrode but not on the exposed cutting edge, the solidified vitreous enamel coating comprising a glass-ceramic composition having a crystalline phase and an amorphous phase, and a coefficient of thermal expansion within less than ±30% of the vitreous enamel-coated metal electrode coefficient of thermal expansion, wherein the vitreous enamel-coated electrosurgical cutting blade exhibits a percent blade width reduction no lower than −12% according to a Blade Width Reduction Test, wherein the Test is performed by manually wearing out the blade on porcine tissue using plasma and a PEAK AEX™ electrosurgical generator from Medtronic operated for 10 minutes at Cut Mode 10 followed by 10 minutes at Coagulation Mode 8, and with the percent blade width reduction being based on the width of the vitreous enamel-coated blade measured before and after the Test.

2. The article of claim 1, wherein the vitreous enamel has a dielectric strength of at least 20,000 volts/mm according to ASTM D149-09.

3. The article of claim 1, wherein the solidified vitreous enamel coating does not exhibit visible cracks or chips after 20 minutes testing in the Blade Width Reduction Test.

4. The article of claim 1, wherein the vitreous enamel has a softening temperature of at least 500° C.

5. The article of claim 1, wherein the vitreous enamel has a softening temperature of at least 700° C.

6. The article of claim 1, wherein the crystalline phase comprises $Ca_2ZnSi_2O_7$ or $Sr_2SiO_4$.

7. The article of claim 1, wherein the vitreous enamel comprises an aluminoborosilicate glass.

8. The article of claim 1, wherein the vitreous enamel is formed from a glass frit comprising $SiO_2$, $B_2O_3$, $Al_2O_3$, and optionally one or more of SrO, BaO, CaO, MgO, ZnO, $Na_2O$, $K_2O$ or a combination thereof.

9. The article of claim 1, wherein the vitreous enamel has a thickness of about 75 μm to about 100 μm.

10. The article of claim 1, wherein the vitreous enamel has a coefficient of thermal expansion of about $6 \times 10^{-6}/°$ C. to about $16 \times 10^{-6}/°$ C. according to ASTM E228.

11. The article of claim 1, wherein the vitreous enamel has a coefficient of thermal expansion of about $10 \times 10^{-6}/°$ C. to about $12 \times 10^{-6}/°$ C. according to ASTM E228.

12. The article of claim 1, wherein the metal electrode is titanium, tantalum, molybdenum, tungsten, stainless steel, or an alloy thereof.

13. The article of claim 1, wherein the metal electrode has a coefficient of thermal expansion of about $10 \times 10^{-6}/°$ C. to about $12 \times 10^{-6}/°$ C. according to ASTM E228.

14. The article of claim 1, wherein the vitreous enamel coating has a coefficient of thermal expansion within ±20% of the metal electrode coefficient of thermal expansion.

15. The article of claim 1, wherein the vitreous enamel coating has a coefficient of thermal expansion within ±10% of the metal electrode coefficient of thermal expansion.

16. The article of claim 1, wherein the vitreous enamel coating has a coefficient of thermal expansion less than the metal electrode coefficient of thermal expansion.

17. The article of claim 1, further comprising an insulated handle attached to the electrosurgical cutting blade and housing at least one conductor that can connect the metal electrode to a radiofrequency energy power supply.

18. The article of claim 1, wherein the vitreous enamel is formed from a glass frit comprising, as molar percentages:

| | |
|---|---|
| $SiO_2$ | 30-50%, |
| $B_2O_3$ | 0.5-15%, |
| $Al_2O_3$ | 0.5-10%, |
| SrO | 5-30%, |
| CaO | 5-30%, and |
| ZnO | 0.5-20%. |

19. The article of claim 1, wherein the electrosurgical cutting blade is a single flattened blade with a rounded edge.

* * * * *